United States Patent [19]
Arnold et al.

[11] Patent Number: 5,541,100
[45] Date of Patent: Jul. 30, 1996

[54] CHIMERIC RHINOVIRUSES

[75] Inventors: Edward V. Arnold; Gail F. Arnold, both of New Brunswick, N.J.

[73] Assignee: Rutgers University, New Brunswick, N.J.

[21] Appl. No.: 304,635

[22] Filed: Sep. 12, 1994

Related U.S. Application Data

[63] Continuation of Ser. No. 41,790, Apr. 1, 1993, abandoned, which is a continuation of Ser. No. 582,335, Sep. 12, 1990, abandoned.

[51] Int. Cl.$^6$ .............................. C12N 7/01; A61K 39/12
[52] U.S. Cl. .................................... 435/235.1; 435/172.3; 424/93.6
[58] Field of Search .............................. 435/235.1, 172.3; 424/93.6

[56] References Cited

FOREIGN PATENT DOCUMENTS 0323900  7/1989  European Pat. Off. .......... C12N 7/00

OTHER PUBLICATIONS

Mizutani, S. et al. (Nov. 1985), J. Virol., vol. 56(2), pp. 628–632.

Panicali, D. et al. (Sep. 1983), Proc. Nat. Acad. Sci, vol. 80, pp. 5364–5368.

Kohara, M. et al. (Aug. 1988), J. Virol., vol. 62(8), pp. 2828–2835.

Evans, D. J. et al. (Jun. 1989), Nature, vol. 339, pp. 385–388.

*Primary Examiner*—Mindy Fleisher
*Assistant Examiner*—Philip W. Carter
*Attorney, Agent, or Firm*—Kenyon & Kenyon

[57] ABSTRACT

Recombinant chimeric human rhinovirus and method for stimulation of a specific immune response. Design considerations, methods, and examples are described. Chimeric rhinoviruses can be used as vaccines and for a variety of other immunotechnological applications.

26 Claims, No Drawings

5,541,100

CHIMERIC RHINOVIRUSES

This application is a continuation of U.S. Ser. No. 08/041,790, filed Apr. 1, 1993, abandoned, which is a continuation of application Ser. No. 07/582,335 filed on Sep. 12, 1990, now abandoned.

FIELD OF THE INVENTION

The invention relates to recombinant chimeric human rhinoviruses which can be used to stimulate an immune response to the chimeric portion of the rhinovirus and thus serve as a broad spectrum of vaccines. Alternatively, the chimeric rhinoviruses can be used to stimulate antibody production for use, for example, in immunodiagnostic systems or for passive immune purposes.

DESCRIPTION OF THE BACKGROUND ART

The production of effective and safe vaccines against harmful viruses and other pathogens continues to be a difficult endeavor. To date, the most successful vaccines involve the use of inactivated viruses or live attenuated viruses obtained from multiple passages of wild-type viruses in tissue culture or in non-human primates. A concern that still lingers, however, is that outbreaks occasionally occur, apparently from improper inactivation of the viruses, reversion or pseudoreversion of the viruses to virulent strains, extension of the host range, and/or contamination of vaccines with live virus.

To overcome some of these complications, considerable research effort has been expended to examine the feasibility and efficacy of immunizing with empty viral capsids and pathogen-derived proteins and peptides. Unfortunately, the antigenicity profiles for complex virions and empty capsids are often quite different. This phenomenon has been documented for several picornaviruses, including rhinovirus (Lonberg-Holm & Yin, *J. Virol.*, 12:114–123, 1973), poliovirus (Mayer, et al., *J. Immunol.*, 78:435–455, 1957), foot-and-mouth disease virus (FMDV) (Rowlands, et al., *J. Gen. Virol.*, 26:227–238, 1975), and Coxsackie B virus (Frommhagen, *J. Immunol.*, 95:818–822, 1965). Studies with individual virion proteins have shortcomings as well. Individual coat proteins, for instance, have antigenic determinants absent from intact viruses (Wiegers & Derrick, *J. Gen. Virol.*, 64:777–785, 1983) and are generally far less effective at stimulating neutralizing antibodies than are whole virions. Attempts to use peptides to provide protection against dangerous pathogens have also been disappointing. Despite occasional examples of success (e.g., Bittle, et al., *Nature*, 298:30–33, 1982; Pfaff, et al., *EMBO. J.*, 1:869–874, 1982), most peptides fail to protect vaccinated animals, even when they are capable of stimulating the production of neutralizing antibodies (e.g., Ada & Skehel, *Nature*, 316:764–765, 1985; Tiollais, et al., *Nature*, 317:489–495, 1985; DiMarchi, et al., *Science*, 232:639–641, 1986).

A more recent approach to vaccine development and the one which is utilized in the present invention uses chimeric viruses or virus-like particles (VLPs) as vehicles for presentation of foreign antigens to the immune system. A number of virus-like particles (VLPs) composed of fusion proteins have been shown to test positively in standard enzyme-linked immunosorbent assays (ELISAs) with antibodies directed against either substituent of the fusion protein. Among chimeric VLPs, almost none have been tested for their ability to protect infected animals; an exceptional case involved the testing of a hepatitis B surface antigen:poliovirus VPI chimera which, when injected into mice, produced only weak protection against poliovirus (Delpeyroux, et al., *Science*, 233:472–475, 1986). Live recombinant viruses with the composite antigenicity of mixed poliovirus types have recently been produced in other laboratories (Kohara, et al., *J. Virol.*, 62:2828–2835, 1988; Martin, et al., *EMBO. J.*, 7:2839–2847, 1988; Burke, et al., *J. Gen. Virol.*, 70:2475–2479, 1989); these reports gave no reference to testing of these live chimeras for protection against the virus. In another experiment, Evans, et al., (*Nature*, 339:385–388, (1989)) incorporated an epitope (positions 735–752) from the transmembrane glycoprotein of HIV-1, gp41, into the neutralizing antigenic region of VPI (NAg-1) of poliovirus 1 Sabin. These workers reported that rabbit antisera and monoclonal antibodies elicited by the chimera were capable of neutralizing in vitro a wide range of American and African isolates of HIV-1. Protection studies were not reported with this construct.

Unfortunately, previously developed chimeric viruses, such as those based on poliovirus and vaccinia virus, have certain characteristics which make them less than ideal. One of the most significant drawbacks to these chimeric viruses is that their effectiveness as vaccines is limited since many individuals already have a significant immune response to the native virus. Also, at least in the case of poliovirus, the use of a live vaccine carries with it the fact that the native virus is a major pathogen with associated risks.

A cDNA clone of HRV14 was reported by Mizutani and Colonno (*J. Virol.*, 56:628, 1985). This clone of HRV14 purportedly has been utilized to make single-site mutations in the coat proteins primarily for the purpose of examining the properties of the cell receptor attachment site on the viral surface (Colonno, et al. 1988). However, successful construction of immunogenic chimeras of HRV14, or any other HRV, have not been reported.

An improved way to stimulate an immune response using a chimeric virus would be to utilize a native virus which, (1) is a relatively mild pathogen, such that little risk would be associated with the use of a live chimeric virus vaccine; (2) has a broad range of serotypic diversity (>100 serotypes), lessening the likelihood of preexisting immunity and thereby enabling vaccination in adults; and (3) has the ability to stimulate a significant neutralizing immune response in mucosal membranes as well as in serum. The present invention provides a means for accomplishing this result.

SUMMARY OF THE INVENTION

The present invention arose out of the discovery that a recombinant chimeric human rhinovirus could be produced which, when introduced into a host, stimulates an immune response in the host to the chimeric portion of the recombinant rhinovirus. These chimeric portions, or regions, are exposed as part of viral surface proteins such that their presence does not prevent the reproduction of the viable virus. The chimeric portion is incorporated into the virus by inserting a nucleotide fragment with a base sequence encoding the chimeric portion into a plasmid used to generate the viral genome such that the inserted nucleotide changes will be expressed as part of the surface protein of the rhinovirus. The chimeric region is exposed and accessible to the immune system of the host being immunized with the chimeric rhinovirus.

DETAILED DESCRIPTION OF THE INVENTION

The present invention comprises at its most fundamental level a recombinantly modified chimeric human rhinovirus.

This rhinovirus can be used to vaccinate a human such that an immune response is produced to the chimeric portion of the rhinovirus. The chimeric rhinovirus also can be used for a variety of other immunotechnological applications, such as stimulating the production of antibodies in animals. Such antibodies can then be used, for example, in immunodiagnostic tests or for passive immunization against disease.

Rhinoviruses are among the major pathogenic agents that cause common colds in humans. There are a number of compelling advantages of using rhinoviruses as live-virus vaccine vectors for human use. Rhinoviruses cause relatively mild and short-term, although annoying, pathogenic symptoms. Rhinoviruses provoke not only a localized mucosal immune response, but also a significant serum immune response. The immune response to rhinovirus infection is long-lasting and can be boosted by reimmunization.

A general misunderstanding persists that HRV infections cause only "superficial" immune responses and HRV-based vaccines would only be relevant and effective for respiratory viral infections. Nasal secretions contain significant neutralizing antibody titers (consisting largely of the IgA subclass) following intranasal (IN) administration of HRVs, and protection against reinfection by homotypic HRV challenge appears to be largely due to the presence of significant IgA neutralizing titers in nasal secretions. In fact, both inactivated HRVs (for example, "killed" by treatment with 0.025% formalin and administered either IN or intramuscularly (IM)) and live HRVs (preferably administered IN) lead to significant neutralizing antibody titers in serum (consisting primarily of IgM and IgG subtypes). While the sensitivities of different tests for measuring neutralizing antibody titers can vary significantly (i.e., by an order of magnitude for poliovirus neutralizing antibody tests (Albrecht, et al., *Rev. Infect. Dis.*, 6:5540–5544, 1984)), a comparison of such titers for HRVs with those for poliovirus (live-attenuated and inactivated poliovirus, both successfully used for vaccination) reveals marked similarity. Indeed, HRVs may stimulate an immune response in a variety of mucosal membranes that could be relevant to a wide variety of diseases.

The production of the chimeric rhinoviruses of the invention can be accomplished using site-directed mutagenesis. This technique involves the hybridization of a mutagenic DNA oligomer encoding the immunogenic chimeric region of choice (employing preferred codon usage for HRV14 wherever possible), with a source of single-stranded template DNA for synthesis of double-stranded plasmid DNA. In cases where single-stranded DNA contains uracil, appropriate bacterial cells can be used to preferentially destroy the uracil-containing strand and replace it with freshly synthesized DNA directed from the mutagenized strand, thus increasing the efficiency of the mutagenesis reaction. It is also possible to utilize such techniques as subcloning and cassette mutagenesis, for instance using polymerase chain reaction (PCR) amplification of mutagenic DNA sequences to be ligated into pWR40.

Mutagenized plasmid DNAs are screened for correctness using restriction digestion analyses, taking advantage of (wherever possible) specific changes in restriction digestion patterns. Labeled nucleic acid probes that are complementary to sequences that have been inserted or removed can also be used to aid in the detection of incorporation of new sequences or loss of old sequences, respectively. Additionally, antibodies can be used to screen potentially mutagenized viruses for incorporation of desired antigens. Apparently correct DNAs are then used as templates for in vitro transcription reactions, taking advantage of a T3 promoter just upstream of the HRV14 sequence in the plasmid. In vitro transcripts are used to transfect HeLa cells (Mizutani & Colonno, *J. Virol.*, 56:628–632, 1985), ideally resulting in production of plaques. Plaques are picked, amplified, and analyzed immunologically. The amplification of single plaques to milligram quantities of virus is best done in a serial fashion, inoculating cells in monolayers with low multiplicities of infection. When the number of monolayers becomes unwieldy, it is most efficient to switch to suspension cultures for large-scale propagations, though the relative yields are reduced. When plaques cannot be obtained, infected cells can either be harvested and chimeric viruses released by multiple freeze/thaw cycles, or, if necessary, the infected cells can be passaged until a variant of the virus succeeds in making plaques. When plaques can be obtained, but are difficult to amplify to high titer, it may be necessary to 1) repeat the mutagenesis using an oligomer with different codon-usage properties, 2) perform propagations in slower growing monolayers of cells, or 3) select for natural variants of the chimera that grow more easily (i.e., that produce larger plaques). Correctness of the most interesting constructions are determined by DNA sequencing of plasmid DNAs (Sanger, et al., *Proc. Natl. Acad. Sci. U.S.A.*, 74:5463–5467, 1977) and by RNA sequencing of chimeric viruses (e.g., Rico-Hesse, et al. *Virology*, 160:311–322, 1987).

The cellular immune response also plays an extremely important role in providing immunity against viruses and other pathogens. Among the components of cell-mediated immune (CMI) response are cytotoxic T-lymphocytes (CTLs), macrophages, and so forth. Chimeric rhinoviruses will also stimulate the cellular immune system in relevant ways that will be beneficial in providing immunity against foreign pathogens. The determinants for optimal stimulation of cellular immunity are less well characterized than for those of the humoral immune response. It is anticipated that T-cell epitopes of foreign pathogens (and other sequences that provoke CMI) can be successfully placed in many portions of the HRV coat proteins in addition to the surface exposed regions. For this purpose, epitopes that provoke CMI can also be inserted into any of the non-structural proteins of the chimeric HRV, such as the polymerase (3D protein) or protease (3C protein) that are also produced in high copy number during infection in the host.

A further advantage of using HRV chimeras for immunization is that 90% of all rhinoviral serotypes ("major" group HRVs) bind to the intercellular adhesion molecule-1 (ICAM-1), which is expressed on many cell types. Along these lines, a particularly useful HRV having ICAM-1 receptor specificity is HRV-14. Among advantages for using HRV14 include the availability of a full-length clone, knowledge of the three-dimensional structure of HRV14 (Rossmann, et al., *Nature*, 317:145–153, 1985; Arnold & Rossmann, *J. Mol. Biol.*, 211:763–801, 1990), and the extensive description of the HRV14 immunogenic surface (Rossmann, et al., ibid, 1985; Sherry, et al., *J. Virol.*, 57:246–257 1986). The other 10% of HRV serotypes ("minor" group HRVs) bind to an, as yet, unspecified cellular receptor. Modification of these HRVs using the methodology of the invention for HRV14 would also yield chimeric vaccines. Examples of minor group HRVs which have been well characterized and could be used in the present invention to produce chimeric rhinoviruses are HRV1A, whose structure has been determined (*J. Mol. Biol.*, 210:91–111, 1989), and HRV2.

One of the tremendous advantages of using chimeric HRVs as vaccines is that multiple serotypes can be utilized.

Thus, if immunity exists or develops to a given serotype, it is possible to use another chimeric HRV from a serotype for which there is no preexisting immunity. There have been at least 100 distinct HRV serotypes identified. Consequently, vaccination can be accomplished for an enormous variety of pathogens in a single individual. This is in sharp contrast to poliovirus, where only three serotypes exist. It is anticipated that eventually all HRVs could be potentially used successfully in this type of strategy (both the major and the minor group HRVs). Furthermore, since each serotype can carry multiple foreign epitopes, the possible arrangements of the epitopes are great. It is likely that simultaneous inoculation of an individual with multiple chimeric HRVs of even a single serotype can successfully immunize against multiple pathogens.

It may be especially advantageous to utilize recombinant chimeric human rhinoviruses when the chimeric portion is a hapten which ordinarily must be coupled to a less effective and sometimes problematic carrier molecule in order to confer immunogenicity. Such recombinant rhinoviruses having the chimeric region on their surface would, by themselves, effectively present this portion in a manner which renders it immunogenic and thereby eliminate the need for such coupling reactions. It should be emphasized that the chimeric region is typically engineered to be in a location of the rhinovirus that, under normal conditions, is immunogenic.

Any epitope, usually of proteinaceous origin, from a source which is capable of inducing an immune response specific to the source can potentially be used in the recombinant chimeric human rhinoviruses of the invention. In order to be effective as a vaccine, the foreign epitope present on the surface of the chimeric rhinovirus should be presented in an immunopotent manner such that components of the host immune system, such as T-cells or B-cells, are stimulated. However, as stated previously, the cellular immune response may be stimulated by foreign peptide sequences inserted at any region of the HRV proteins (coat proteins or otherwise), regardless of surface exposure.

Useful antigens for substitution in the recombinant chimeric human rhinoviruses can be identified by various criteria, such as the involvement of the antigen in neutralization of pathogenic infectivity, type or group specificity, recognition by patient antisera, and/or the presence of protective effects of antisera generated to the antigen. Desirably, an epitope derived from the antigen would display minimal antigenic variation with time. The genetic sequence encoding the epitope constituting the chimeric region of the chimeric rhinovirus may be obtained by techniques known to those of skill in the art such as by recombinant DNA techniques for plasmid DNA or cDNA reverse transcribed from genomic viral RNA or by chemical synthesis.

The recombinant chimeric human rhinoviruses have potential uses as vaccines for diseases and disorders wherein the source of the chimeric region is derived from a viral, neoplastic, parasitic, or bacterial source. Numerous viral-specific antigens are known to those of skill in the art and can potentially be incorporated into the chimeric rhinoviral vaccines of the invention. For example, such antigens, or portions thereof, which encode the epitope(s) include such sources as influenza A hemagglutinin; hepatitis A virus VP1 and VP3; hepatitis B surface, core, or E antigens; poliovirus capsid protein VP1, VP2, and VP3; rabies virus glycoprotein; retroviral envelope glycoproteins or capsid proteins; foot and mouth disease virus VP1; herpes simplex virus glycoprotein D; Epstein-Barr virus glycoprotein; pseudorabies virus glycoproteins; vesicular stomatitis virus glycoprotein, to name a few. Bacterial antigens that can be incorporated include those from the genera Pneumococcus, Salmonella, Shigella, Clostridia, Pseudomonas, Streptococcus, Staphylococcus, and Neisseria, to name a few. Parasitic antigens that can be presented on the chimeric rhinoviruses include those from the genera Trypanosoma, Leishmania, Plasmodium, and Toxoplasma, to name a few. Neoplastic antigens that can be displayed on the chimeric rhinoviruses include those from tumors and carcinomas (e.g., mammary, colon) and those from oncogene products or mutated oncogene products (e.g., ras, myc).

Human rhinovirus 14 (HRV14), and other HRV serotypes, are called common cold viruses because they are among the most commonly isolated viruses from humans experiencing mild respiratory illness. The virus is composed of 60 protomers related by icosahedral symmetry, each containing a single copy of each of four polypeptide chains VP1, VP2, VP3, and VP4. A single, positive strand of RNA, which is translated into a single precursor and then processed into its structural and functional components, is surrounded by the protein capsid. The three-dimensional structure of the HRV14 capsid has been solved (Rossmann, et al., *Nature*, 317:145–153, 1985) and refined (Arnold & Rossmann, *Acta Cryst.*, A44:270–282, 1988) at 3.0Å resolution by X-ray crystallography.

The complete nucleotide sequence of HRV14 is known (Stanway, et al., *Nucl. Acids Res.*, 12:7859–7875, 1984; Callahan, et al., *Proc. Natl. Acad. Sci. U.S.A.*, 82:732–736, 1985). The major coat proteins, VP1, VP2, and VP3, form the surface of the virion and are recognized by the immune system. Structurally, these proteins are very similar to one another (Rossmann, et al., *Nature*, 317:145–153, 1985) sharing a common 8-stranded β-barrel structure. The differences among the coat proteins are manifested almost exclusively as loops with an irregular secondary structure that embellish the basic β-barrel motif where the neutralizing immunogenic sites are located primarily in these loops.

HRV14 has four neutralizing immunogenic sites defined by the locations of amino acid changes that enable the virus to escape neutralization by antibodies (Rossmann, et al., *Nature*, 317:145–153, 1985; Sherry & Rueckert, *J. Virol.*, 53:137–143 (1985); Sherry, et al., *J. Virol.*, 57:246–257, 1986). These neutralizing immunogenic sites, abbreviated NIms, designate the viral coat protein from which they are primarily derived. Thus, NIm-IA and NIm-IB are located primarily on VP1, and NIm-II, and NIm-III are located primarily on VP2 and VP3, respectively.

Human rhinoviruses have major advantages as vaccine vehicles over those that are currently in use. Rhinoviral pathology is typically mild (as shown in thousands of experimental infections in humans) and HRVs are high molecular weight carriers of multiple immunogenic sites capable of replicating in the host and provoking a high titer antibody response. The HRV14 serotype is particularly useful since this system offers: a high resolution three-dimensional refined structure; a well mapped immunogenic surface; and availability of a cDNA clone. The suitability of HRV14 for chimeric virus construction is illustrated herein by examples showing the successful construction of an HRV14:poliovirus 3 Sabin chimera (substituted at NIm-IA), an HRV14:influenza hemagglutinin chimera (substituted at NIm-II), and HRV14:HIV-1 chimeras substituted at NIm-IA.

Since the rules of protein folding, assembly of macromolecules, and immune recognition and function are not yet known, the viability, antigenicity, and immunogenicity of recombinant chimeric human rhinoviruses could not be assumed prior to a clear demonstration of their construction. This work has demonstrated conclusively for the first time that it is possible to create chimeric HRVs that grow well and have potent antigenicity and immunogenicity profiles, making them excellent candidates for vaccine development.

Preferred in the present invention for stimulation of the humoral immune response are chimeric rhinoviruses wherein the chimeric portion is located at one or more of the four known distinct neutralizing immunogenic sites of the rhinovirus. More than one chimeric region may be substituted, thereby allowing a broader repertoire of stimulation of the immune system. Especially preferred, based on studies thus far, are chimeric substitutions occurring at the NIm-IA and NIm-II sites, since these sites display greater natural sequence variability among natural isolates than the NIm-IB and NIm-III sites and are therefore expected to more easily allow substitutions.

As previously stated, the size of the substituted chimeric region should be sufficient to induce an immune response in the host, but not of a size or of a chemical nature which would prevent proliferation of the virus or cause disruption of the virus. The substituted chimeric region is usually from immunization (Urakawa, et al., *J. Gen. Virol.*, 70:1453–1463, 1989). The use of this latter system to produce the chimeric HRVs of the present invention could be especially valuable since generation of large quantities of vaccine material would not depend upon the compatibility of the foreign sequences with HRV reproduction requirements.

Table 1 lists various surface-exposed regions of the various NIm sites, as well as other surface regions, that will tolerate replacement of native sequences with chimeric sequences. The choices of residues defining a region, or region to be replaced, are approximate, based on a combination of quantitative structural assignments (such as those corresponding to secondary structural elements) and an understanding of the HRV14 structure. Optimal replacements depend on desired application. The listed nomenclature follows that of Rossmann, et al., (*Nature*, 317:145–153, 1985) and Arnold and Rossmann (*J. Mol. Biol.* 211:763–801, 1990). Residues in the viral proteins have been enumerated XYYY, where X corresponds to the viral protein number (VPX) and YYY the residue number within chain X.

TABLE 1

CANDIDATE SURFACE-EXPOSED HRV14 REGIONS FOR PLACEMENT OF CHIMERIC REGIONS

| | LOCATIONS OF ESCAPE MUTATIONS | RESIDUES IN REGION | RESIDUES REPLACED | | |
|---|---|---|---|---|---|
| | | | LARGE | INTERMEDIATE | SMALL |
| I. NIm sites | | | | | |
| A. NIm-IA | 1091, 1095 | 1082–1099 | 1082–1099 | 1085–1096 | 1091–1095 |
| B. NIm-IB | 1083, 1085 | 1079–1089 | 1079–1089 | 1081–1087 | 1082–1086 |
| | 1138, 1139 | 1134–1143 | 1134–1143 | 1135–1141 | 1136–1140 |
| C. NIm-II | 2158, 2159, 2161, 2162 | 2155–2169 | 2155–2169 | 2157–2165 | 2158–2162 |
| | 2136 | 2132–2140 | — | 2132–2140 | 2134–2138 |
| | 1210 | 1206–1214 | — | 1206–1214 | 1208–1212 |
| D. NIm-III | 3072, 3075, 3078 | 3068–3082 | 3068–3082 | 3070–3080 | 3072–3078 |
| | 3203 | 3199–3207 | — | 3199–3207 | 3201–3205 |
| | 1287 | 1283–1289 | — | 1283–1288 | 1284–1288 |
| II. Other surface regions | | | | | |
| A. VP3 "knob" | — | 3053–3069 | 3053–3069 | 3057–3065 | 3058–3062 |
| B. FMDV loop | — | 1200–1221 | 1200–1221 | 1206–1214 | 1208–1212 |
| C. VP2 BC loop | — | 2070–2078 | — | 2070–2078 | 2072–2076 |
| D. VP1 C-terminus | — | 1255–1289 | 1255–1289 | 1265–1280 | 1270–1275 |
| E. VP2 C-terminus | — | 2254–2262 | — | 2254–2262 | 2258–2262 |
| F. VP3 C-terminus | — | 3222–3236 | — | 3227–3236 | 3230–3236 | about 5 to about 300 amino acids, preferably from about 5 to about 50 amino acids, most preferably, from about 5 to about 30 amino acids. In selecting chimeric regions for substitution, it should also be kept in mind that the optimal size of the chimeric region, at least in terms of substitutions made at the neutralizing immunogenic sites, may vary somewhat with a particular site. The substituted chimeric region may consist of non-contiguous segtments of amino acids as do some of the native NIm sites.

It should noted that for some of the larger substitutions, it is possible for a relatively small segment of the rhinovirus surface (for example, 5–20 amino acids) to be replaced by as much as several hundred amino acid residues. A modification corresponding to a net insertion of more than about 100 amino acids may require deletion of a similar amount at a different site in the rhinoviral genome to avoid generating a vital genome that is too large to package. Alternatively, an expression system such as baculovirus could be used to generate non-infectious empty capsids that are useful in The specific chimeras described in the examples involve alteration of the NIm-IA and NIm-II regions of HRV14. While the NIm-IB and NIm-III regions of the virus also have variable amino acid composition (as one would expect for immunogenic sites), the sequence alignments reveal less variation in chain lengths for these regions in different picornaviruses. On the other hand, the NIm-IA and NIm-II regions are characterized by diversity for both amino acid sequence and chain length, suggesting that they would be more likely to accommodate a greater variety of foreign sequences than either NIm-IB or NIm-III. However, it is anticipated that the majority of the surface of HRV14 is immunogenic when used for chimeric constructs of the nature described herein.

Amino acid sequence and computer graphic analysis of the neutralizing immunogenic site II (NIm-II) indicated that a protruding loop comprising amino acids 157–166 of VP2 on HRV14 would be an ideal candidate for replacement by foreign antigens. A chimeric virus containing an influenza hemagglutinin (HA) immunogenic sequence in the place of the NIm-II loop was constructed by applying recombinant DNA techniques to a plasmid containing a cDNA representation of the full-length HRV14 genome. The resulting chimeric HRV14:influenza HA (HRV14:HA) was tested for loss of NIm-II antigenicity and for introduction of influenza antigenicity. As expected, monoclonal antibodies directed against the NIm-II site of HRV14 do not neutralize HRV14:HA, which indicates that there is loss of recognition of this site. Neutralization tests performed with polyclonal antisera against four relevant strains of influenza HA show that three of the four antisera have significant, even moderate (reciprocal neutralizing titers of 30–300), neutralizing activity on the HRV14:HA chimera.

The escape mutations that define the NIm-IA site (VPI residues 91 and 95) are found within a 14-amino acid structural unit that can be classified as an ω-loop (Leszczynski & Rose, *Science*, 234:849–855, 1986) which pinches together at its termini. The NIM-IA loop is relatively compact and self-contained, and the majority of the short contacts that it has with the rest of the capsid occur in the terminal residues. This, together with the fact that the loop termini form a piece of the conserved β-barrel structure, suggests that these termini function as "anchor points" onto which foreign stretches of peptide may be introduced without greatly perturbing the function of the virus. The NIm-II site has a more complex structure than the NIm-IA loop and is a discontinuous epitope. The escape mutations that define the NIm-II site (VP2 residues 158, 159, 161, 162, and 135, and VPI residue 210) are located on three non-contiguous stretches of peptide in the VP2 and VP1 proteins (Rossmann, et al, ibid, 1985; Sherry, et al., *J. Virol.*, 57:246–257, 1986). The highest density of escape mutations in NIm-II occurs on a loop that includes residues 150 to 168 of VP2. Structure and sequence information suggests that VP2 Ser157 (directly preceding the escape mutations) and VP2 Pro 165 (following the escape mutations and well-conserved among polioviruses, Coxsackie viruses, and rhinoviruses) serve as "anchor points" for the modular replacement of intervening amino acids. Alignments of NIm-II of HRV14 with other rhinoviruses and polioviruses indicates that at least seven more amino acids can be tolerated in this region than are present in HRV14, and thus large immunogenic insertions are possible at this location. However, compensatory changes may have to be considered in the neighboring protein environment in some of the chimeric constructs to enable the viral protein shell to fold and function properly. By taking advantage of the knowledge of the three-dimensional structure of HRV14 and, wherever possible, that of the transplanted antigens, it is possible to avoid grafting sequences blindly into important structural elements that could disrupt the functions of the virus or result in poor antigen presentation.

The NIm-III and NIm-IB sites are also discontinuous epitopes. The escape mutations defining the NIm-III site (VP3 residues 72, 75, 78, and 203, and VP1 residue 287) are located in three distinct polypeptide segments that are spatially adjacent. The escape mutations that define the NIm-IB site (VP1 residues 83, 85, 138, and 139) are located on two adjacent polypeptide segments in a protruding region near the five-fold axis of icosahedral symmetry of the rhinovirus. While the length and composition of NIm-IB and NIm-III in different picornaviruses are more conserved than for NIm-IA and NIm-II, each of the NIm sites is favorable for replacement in constructing the chimeric HRVs of the invention.

In an embodiment illustrated herein, a chimeric virus was successfully produced by recombinant modification of a human rhinovirus (HRV14) in which the NIm-II loop was replaced with a neutralizing immunogen from the orthomyxovirus, Influenzavirus. In this instance, the immunogen was selected from the influenza hemagglutinin which naturally bears a conformational resemblance to one of the prominent loops of the NIm-II transplantation site of HRV14. It was thought that selecting such a region would enhance the likelihood that the influenza HA sequence would adopt a conformation recognizable by and capable of inducing, neutralizing antibodies against influenza. This sequence was also of special interest because it is located at the periphery of the sialic-acid binding pocket of influenza HA that is believed to be involved in receptor attachment. The HRV14:HA chimera was generated based on the mutagenesis methods of Kunkel, et al. (*Meth. Enzymol.*, 154:367–381, 1987). The resulting chimeric HRV14:influenza HA was tested for loss of NIm-II antigenicity and for introduction of influenza antigenicity and growth characteristics.

In other specifically exemplified embodiments of the invention, an antigenic segment of a picornavirus was substituted at an alternate immunogenic neutralization site of HRV, In this case, the NIm-IA loop of HRV14 was replaced by the NAg-1 site of poliovirus. In addition, the inventors have produced chimeric rhinoviruses displaying antigenic segments from human retroviruses as exemplified by HIV. The HIV chimeric rhinoviruses involve substitution of portions derived from the gp120 and gp41 HIV-1 glycoproteins. The HIV-1 chimeric regions were substituted at the NIm-1A site of HRV14.

The chimeric rhinovirus to be used in this invention can be generated from a stable source of plasmid DNA, or later from seed stocks of the chimeric HRV. Using the techniques described, the recombinant chimeric human rhinoviruses generated will have the exact desired sequence content and length of amino acids and will not have any undesired amino acids that could result from using a restrictive mutagenesis cassette. When the chimeric HRV is to be produced in large amounts, large numbers of cells can be accommodated either in suspension cultures and/or on carriers such as microcarrier beads. Propagations can be performed in transformed human cells, such as the H1-HeLa cells used in this work, or preferably in non-transformed human cells, such as human diploid fibroblast cells (WI-38, MRC-5, etc.). Virus can be obtained in purified form from infected cells following cell lysis. Examples of purification steps include standard differential centrifugation techniques, concentration by ultrafiltration or pressure dialysis, or concentration by precipitation.

According to the present invention, a vaccine for stimulating an immune response to the chimeric region comprises a recombinant chimeric human rhinovirus and an inert pharmaceutically acceptable carrier or diluent. Preferably the carrier or diluent is one compatible with vaccine administration by mass administration techniques. However, the carrier or diluent may also be compatible with other administration methods such as injection, eye drops, nose drops, and the like.

The vaccine according to the present invention is administered in amounts sufficient to stimulate the immune system against the chimeric portion of the HRV. Preferably, the vaccine is administered in dosages ranging from about $10^2$ to about $10^8$ $TCID_{50}$, preferably from about $10^3$ to about $10^6$ $TCID_{50}$. Since the live chimeric virus replicates in the host, smaller doses may be possible.

The vaccine containing inactivated recombinant chimeric human rhinovirus according to the present invention is administered in amounts sufficient to stimulate the immune system against the chimeric portion of the virus. Preferably, the vaccine is administered in dosages ranging from about 10 ng to about 100 µg, preferably between about 100 ng to about 10 µg.

The chimeric rhinoviruses when used as a vaccine usually do not require adjuvants since HRV is a large molecular aggregate capable of stimulating a robust immune response on its own. However, if desired, the vaccines of the present invention may also contain one or more adjuvants. This is especially true when an inactive vaccine is utilized. Any suitable adjuvant can be used including chemical and polypeptide immunostimulants which enhance the response of the immune system to antigens. Preferably, adjuvants such as aluminum hydroxide, aluminum phosphate, plant and animal oils, and the like are administered with the vaccine in amounts sufficient to enhance the immune response to the chimeric portion of the recombinant HRV. The amount of adjuvant added to the vaccine will vary depending on the nature of the adjuvant, generally ranging from about 0.1 to about 100 times the weight of the recombinant chimeric human rhinovirus, preferably, from about 1 to about 10 times the weight of the recombinant chimeric human rhinovirus.

The vaccines of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate, and the like. A stabilizer is particularly advantageous when a dry vaccine preparation is prepared by lyophilization.

The vaccine can be administered by various routes including nasally, ophthalmically, by injection, by exposure, or by any suitable method. A vaccine containing inactivated recombinant chimeric human rhinovirus according to the present invention can be administered by injection. When administered by injection, the vaccines are preferably administered parenterally. Parenteral administration as used herein means administration by intravenous, subcutaneous, intramuscular, or intraperitoneal injection.

While the disclosure above generally describes the present invention, a more complete understanding can be obtained by reference to the specific Examples which follow. The Examples are provided only for purposes of illustration and are not intended to limit the scope of the invention.

EXAMPLE 1

Chimeric Rhinovirus Displaying Influenza Hemagglutinin Antigen

An immunogenic chimera of HRV14 displaying an immunogen from influenza hemagglutinin (HA) was constructed via site-specific mutagenesis of the HRV14 cDNA clone pWR40. Single-stranded DNA generated from the HRV14 cDNA plasmid was hybridized to a single-stranded synthetic oligonucleotide that is complimentary at the NIm-II borders, but that encodes the influenza HA sequence.

A graphical representation of the refined coordinates of HR14 showed that a 10 amino acid loop corresponding to neutralizing immunogenic loop II (NIm-II), corresponding to VP2 residues 157–166, protrudes from the surface of the virus. Sequence alignment of picornaviruses revealed that this region is among the most highly variable portions of the capsid proteins, indicating a likelihood for accommodating foreign sequences without causing gross disruption of the viral capsid structure. The NIm-II structure on HRV14 represents a discontinuous epitope that includes segments of polypeptides from both VP2 and VP1. In this embodiment of the invention, the section of NIm-II that is both highly protruding from the virion surface and most highly exposed (Arnold & Rossmann, *J. Mol. Biol.*, 211:763–801, 1990), and that contained the highest density of mutations in an analysis of spontaneously arising mutants of HRV14 that survive in the presence of monoclonal antibodies that react with NIm-II, was replaced with the chimeric sequence.

A crude conformational matching of this region with influenza hemagglutinin (HA) identified a similarly protruding immunogenic loop with some conformational resemblance. Notably, the two HA residues that did not match well conformationally were both glycines, characterized by conformational flexibility (and residues in common between the sequences).

| HRV14 | (157) | SSANEVGGP | (165) |
| Influenza HA | (128) | TGVTQNGGS | (136) |
| HRV14:influenza HA | | SGVTQNGGP | |

The mutagenesis also introduced two new unique restriction sites at the two ends of the NIm-II loop to simplify further modifications and characterization. The chimeric cDNA plasmid was then used as a template for in vitro synthesis of viral RNA as a source of virion production. Single plaques were recovered from transfected monolayers of HeLa cells and then amplified. The successful construction of the HRV14:HA NIm-II chimera demonstrates that the NIm-II site is a good target for engineering and replacement by foreign sequences and that substitutions at this site can be recognized by antibodies directed against the new chimeric sequence. The HRV14:HA NIm-II chimera has also been crystallized, emphasizing the high degree of homogeneity of the chimeric rhinovirus.

A. Materials and Methods

Wild-type HRV14 virus and H1-HeLa cells were obtained courtesy of Drs. R. R. Rueckert (University of Wisconsin) and M. G. Rossmann (Purdue University). Wild-type and chimeric viruses were grown in H1-HeLa cells, which are adapted for rhinovirus growth (Conant and Hamparian, *J. Immunol.*, 100:107–113, 1968). Viruses were plaque-assayed using R-19 HeLa cells (Abraham and Colonno, *J. Virol.*, 51:340–345, 1984). Mutagenesis was performed on a plasmid derived by inserting a full-length cDNA clone of HRV14 into the HindIII and HincII sites of the pBS phagemid (Stratagene Cloning Systems) to produce pWR40, a gift from W. M. Lee and R. R. Rueckert (Univ. of Wisconsin). The *E. coli* strain used for transformation and plasmid preparation was JM83 (Gene, 33:103–119, 1985), obtained from Dr. P. Maliga (Waksman Institute).

Restriction enzymes ApaI, ClaI, SmaI, and T3 RNA polymerase were purchased from Bethesda Research Laboratory (BRL). T4 DNA polymerase was purchased from Boehringer Mannheim Biochemicals. T4 polynucleotide kinase was purchased from New England Biolabs. Ribonuclease inhibitor RNasin was obtained from Promega Corporation. Ribonucleotide triphosphates, deoxynucleotide triphosphates, and dideoxynucleotide triphosphates were purchased from Pharmacia LKB Biotechnology. Radioactive isotopes were obtained from NEN/DuPont.

Anti-HRV14 guinea pig serum was purchased from American Type Culture Collection (ATCC, NIAID v-103-501-558). Monoclonal antibodies against the HRV14 NIm-II site were gifts from A. G. Mosser and R. R. Rueckert (University of Wisconsin). Anti-influenza HA serum was a gift from Dr. R. Webster (St. Jude Children's Research Hospital, Memphis, Tenn.).

B. Construction of Plasmid

Single-stranded DNA was produced from pWR40 based on the method of Kunkel (*Proc. Natl. Acad. Sci., U.S.A.*, 82:488–492, 1985; Kunkel, et al., *Meth. Enzymol.*, 154:367–382, 1987). A 50 nucleotide oligomer encoding the desired immunogenic sequence from the influenza hemagglutinin as well as two unique restriction sites (recognized by the enzymes ApaI and ClaI) was synthesized, deprotected, and further purified on an 8% polyacrylamide sequencing gel. The major and slowest migrating band was isolated and extracted (with 0.5M ammonium acetate, 1 mM EDTA overnight at 37° C.), precipitated in 70% ethanol and resuspended in TE buffer (10 mM Tris-HCl, pH 7.4, 1 mM EDTA). Oligomer was phosphorylated in the presence of 100 mM Tris-HCl, pH 7.5, 10 mM $MgCl_2$, 1 mM DTT, 0.1 mM EDTA, 1 mM spermidine, 1 mg/ml BSA, 1 mM ATP, and 10 units of T4 polynucleotide kinase. Free nucleoside triphosphates were then removed using Sephadex G-25 (Pharmacia) in a Spin-X centrifuge filter unit (Costar).

Mutagenesis was performed by hybridizing 10 pmol of phosphorylated, mutagenic oligomer to 1 pmol of single-stranded pWR40 DNA, then synthesizing the second strand by adding 20 mM HEPES, pH 7.8, 2 mM DTT, 2 mM $MgCl_2$, 0.5 mM each of dATP, dCTP, dGTP, and dTTP, 1 mM ATP, 10 units of T4 DNA polymerase, and 400 units of T4 DNA ligase.

A small amount of the mutagenesis mixture was used to transform competent JM83 cells (method of Kushner in Maniatis, et al., *Molecular Cloning*, Cold Spring Harbor Laboratory, Cold Spring Harbor, N.Y., 1982). Isolated transformant colonies were grown in LB medium (Miller, *Experiments in Molecular Genetics*, Cold Spring Harbor Laboratory, Cold Spring Harbor, N.Y., 1972). Crude preparations of DNA were prepared by the method of Serghini, et al. (*Nucleic Acids Res.*, 17:3604, 1989) and screened for correctness of size and restriction pattern. Apparently correct clones were subsequently prepared in larger and purer quantities (using Circle-Prep™, Bio 101) to provide substrates for DNA sequencing and in vitro transcription. DNA sequencing was performed using the Sanger dideoxy method (Sanger, et al., *Proc. Natl. Acad. Sci.*, 74:5463–5467, 1977). RNA sequencing was performed using reverse transcription to generate DNAs that were subsequently sequenced.

The plasmid containing the influenza hemagglutinin neutralizing immunogen, pWR40:HA, was linearized outside of the HRV14-encoding sequence with the restriction enzyme SmaI to generate templates for in vitro transcription. According to the methods of Mizutani and Colonno (*J. Virol.*, 56:628–632, 1985), 1 μg of DNA was incubated for 1 hour at 37° C. in the presence of 40 mM Tris-HCl, 8 mM $MgCl_2$, 25 mM NaCl, 2 mM spermidine, 5 mM DTT, 2 mM each of the ribonucleoside triphosphates, 50 units of the ribonuclease inhibitor, RNAsin, and 250 units of T3 RNA polymerase (total volume of 50 μl), yielding typically 50 μg of viral RNA transcripts. Formaldehyde agarose gel electrophoresis revealed a single band of RNAs of the expected length of 7.2 kb, corresponding to full-length genomic RNA.

C. Production of Chimeric Viruses

In vitro synthesized RNAs were prepared for transfection according to Mizutani and Colonno (ibid). After boiling at a variety of dilutions for 2 minutes in $H_2O$ and immediately placing on ice, samples of 12 μl were mixed with 400 μl of ice-cold IRA buffer (10 mM HEPES, pH 7.3, 0.14M LiCl, 1 mM $MgCl_2$, and 1.2 mg/ml DEAE-dextran). 200 μl of each mixture were plated in duplicate on monolayers of HI-HeLa cells and incubated for 20 minutes at 34° C. The plates were then overlaid with 0.5% agar in PA medium and incubated at 34° C. for 72±6 hours. To visualize plaques, plates were stained with 0.03% Neutral Red-containing PBS and incubated at 34° C. for 1 hour. Infectious virus was recovered from plaques by picking them individually into 600 μl of PA medium with sterile pasteur pipettes and freezing and thawing samples rapidly three times. The specific infectivity was found to be about 500 plaque-forming units (PFU)/μg transcript. Plaque assays revealed that, as for pWR40, a single plaque generated from pWR40:HA contained $10^4$–$10^5$ PFU. Viruses from isolated plaques were amplified in HI-HeLa cells by the scheme shown in Table 2.

TABLE 2

AMPLIFICATION OF HRV14:HA CHIMERIC VIRUS

| STAGE OF AMPLIFICATION | INOCULUM SOURCE | $MOI^a$ | PROPAGATION TIME (HOURS) | TOTAL $OUTPUT^b$ | FOLD AMPLIFICATION |
|---|---|---|---|---|---|
| 1. single plaque transfection | RNA | — | 72 ± 6 | $10^4$–$10^5$ | — |
| 2. infected$^c$ monolayer | 50% of stock from (1.) | $10^{-4}$–$10^{-3}$ | 33–48 | $10^6$–$10^8$ | 500–1000 |
| 3. infected monolayers (10–15 150 mm dia. dishes, until 50–80% CPE observed) | 50% of stock from (2.) | $10^{-2}$–$10^{-1}$ | 33–48 | $10^9$–$10^{10}$ | 500–1000 |
| 4. suspension propagation$^d$ (for two multiplication cycles) | 25–50% of stock from (3.) | $10^{-1}$–$10^{-0}$ | 23 | $10^{11}$ | 20–40 |
| 5. suspension propagation$^d$ (for one viral multiplication cycle) | 20–30% of stock from (4.) | 2–5 | 10.5 | $10^{11}$ | 3–5 |

$^a$Multiplicity of infection
$^b$Plaque-forming units (PFU)
$^c$150 mm dia. dish; until primary cytopathic effect (CPE) observed
$^d$In a 4 l Ehrlenmeyer Flask D. Characterization A neutralization assay of HRV14 was performed in quadruplicate by mixing $10^4$ PFU of virus with various dilutions of antibodies in a 96-well microtitration plate and incubating at room temperature for 1 hour. $10^4$ HI-HeLa cells then were added into each well and incubated at 34° C. for 64–72 hours at which time each well was stained with 50 µl of 0.1% crystal violet for 10 minutes and washed twice with water. The neutralizing titer was defined as the reciprocal of the antibody dilution that corresponded to cytopathy of approximately 50% of the cell monolayer.

In order to determine the growth curve of HRV14, $2.5\times 10^5$ HI HeLa cells in 1 ml of M medium were seeded into a 2 cm² well of 24 well tissue culture plate (Cat #4550-03524, Bellco Biotechnology) and incubated at 34° C. in 0.5% $CO_2$ for 16 hours. Medium was aspirated off and $2.5\times 10^5$ PFU (in 0.2 ml of M medium) of wild-type or chimeric virus were added onto the monolayers and plates were incubated at room temperature for 1 hour for viral attachment. Medium was aspirated off and monolayers washed with 0.5 ml of PBS. 1.0 ml of M medium was added into the well and then incubated for 0, 0.5, 1, 2, 4, 7, 10, 12, 16, and 24 hours. Medium was collected and the monolayer was washed with 0.125 ml of PBS. 1.25 ml of M Medium was then added into each well. Both the cell monolayer and growth medium were collected and frozen at −80° C. until they could be subsequently titered for virus production.

Immunologic assays were performed on the chimeric HRV14:HA wherein the influenza HA NIm site had been transplanted at the HRV14 NIm-II site. The chimera was tested by three groups of antibodies for their neutralizing activities (Table 3).

TABLE 3

ANTI-INFLUENZA HA SERA NEUTRALIZE
CHIMERIC HRV14:HA BUT NOT NATIVE HRV14

| Antiserum | RECIPROCAL OF NEUTRALIZING TITERS[a] | |
|---|---|---|
| | Wild-Type HRV14 | Chimeric HRV14:HA |
| Anti-HRV14 serum | 14,125 | ≧56,230 |
| Anti-NIm-II MAb 1 | 2240 | 110 |
| Anti-NIm-II MAb 2 | ≧12,200 | ≦7 |
| Anti-Influ HA serum 1 | ≦7 | ≦7 |
| Anti-Influ HA serum 2 | ≦7 | 890 |
| Anti-Influ HA serum 3 | ≦7 | 270 |
| Anti-Influ HA serum 4 | ≦7 | 40 |

[a]The reciprocal of the antiserum dilution causing the viral cytopathic effect to decrease by 50%.

The chimeric HRV14:influenza HA was tested for loss of NIm-II immunogenicity and for introduction of influenza immunogenicity. Monoclonal antibodies directed against the NIm-II site of HRV14 either failed to neutralize HRV14:HA altogether, or showed only 3% residual neutralizing activity, which indicated that there was loss of recognition of this site. Neutralization tests performed with polyclonal antisera against four relevant strains of influenza HA showed significant, even moderate (reciprocal neutralizing titers of 30–300), neutralizing activity against the HRV14:HA chimera by three of the four antisera. Plaque reduction assays were also performed with the anti-influenza HA sera and showed similar results.

As a positive control, anti-HRV14 guinea pig serum was used to neutralize both wild-type and chimeric virus. Surprisingly, the polyclonal antiserum directed against wild-type HRV14 has stronger neutralizing activity against chimeric HRV14:HA, which has lost one out of four neutralizing antibody binding sites present on the wild-type virus. These experimental results show that the influenza HA antigen has been expressed on the chimeric HRV14 surface and continues to be antigenic in this new context.

EXAMPLE 2

Chimeric Rhinovirus Displaying Poliovirus Antigen

Using the basic techniques described in Example 1, a chimeric virus-encoding plasmid was constructed which utilized the immunodominant neutralizing epitope, NAg-1, from poliovirus type 3 Sabin. This epitope was substituted for NIm-IA, the analogous site on HRV14. This alteration allowed the production of virions, thus demonstrating that the NIm-1A site may also be used as a target for immunogen replacement for the chimeric region.

This particular chimera was chosen because of the structural similarity of the capsid proteins and sequence similarity of the two viruses. As in the case of the HRV14:HA chimera, the HRV14:poliovirus 3 Sabin chimera was generated based on the mutagenesis method of Kunkel (Kunkel, et al. *Proc. Natl. Acad. Sci., U.S.A.*, 82:488–492, 1985; *Meth. Enzymol.*, 154:367–381, 1987). However, in this construct the immunogen was replaced on the surface of VP1 (shown in brackets below), including the residues that define the NIm-IA site. The type 3 sequence was chosen for this construct, since cases of type 2 and 3 poliomyelitis still occur.

| HRV14 | IQN KDATG | IDNHREA KLF |
|---|---|---|
| polio 3 Sabin | VDN EQPT | TRAQ KLF |
| polio 2 Lansing | VDN DAPT | KRAS KLF |
| HRV14:polio 3 Sabin | IQN EQPT | TRAQ KLF |
| HRV14:polio 2 Lansing | IQN DAPT | KRAS KLF |

The site-specific mutagenesis method used involved the hybridization of single-stranded pWR40 DNA with a mutagenic DNA oligomer encoding the NAg-1 loop of poliovirus 3 Sabin. After complete synthesis of the second strand, plasmids were ligated and used for transformation of the JM83 strain of *E. coli*. The plasmid DNAs from 50 transformant colonies were isolated and analyzed by restriction enzyme analysis. Correctness of plasmid and fragment sizes and the presence of a deliberately introduced unique ApaI restriction site in the polio NAg-I DNA were used to identify two apparently correct DNA representations of this chimera. More highly purified DNA samples of both of the recombinant plasmids were prepared and used for DNA sequencing as well as for templates for in vitro transcription following their linearization with the restriction enzyme SacI. The RNAs obtained were then used to transfect HI-HeLa cells. For both apparently correct DNA constructs, virus plaques were isolated. Preliminary experiments with polyclonal antisera directed against poliovirus 3 Sabin (American Type Culture Collection) indicated that the antisera specifically cause neutralization of the HRV14:polio 3 Sabin construct without causing non-specific neutralization of wild-type HRV14.

EXAMPLE 3

Chimeric Rhinovirus Displaying HIV Antigen

Chimeric viruses containing regions derived from the env glycoproteins were prepared using the methodology described in Example 1. These substitutions were made at the NIm-IA site of HRV14.

An HRV14:HIV gp120 chimeric virus was prepared utilizing the principal neutralizing domain of HIV-1 gp120 which resides in a region that is variously referred as to the "V3 loop" (for third variable domain), the immunodominant loop, or the "cysteine loop" of gp120. The presentation of the V3 loop of the MN isolate of HIV-1 appears to be closely related in as many as 50% of over 200 individual isolates of HIV-1 that have been sequenced in this region. Thus, immune stimulation to this region when present in a chimeric rhinovirus should stimulate an immune response which would react with and neutralize a significant portion of HIV-1 strains which are present in the population. This construct has the following chimeric substitution in the HRV14 NIm-IA site:

| HRV 14 | IQN | KDATG | IDNHREA | KLF |
|---|---|---|---|---|
| HIV gp120 MN loop polypeptide | | | IHI GPGRAF | |
| HRV14:HIV gp120 MN | IQN | | IHI GPGRAF | KLF |

The multiple substitution sites available in the HRV system create the potential for applying a "cocktail" approach to generating group-specific vaccines for HIV. Thus, an individual could be immunized with a mixture of viruses substituted at one site or, alternatively, with a single population of chimeric virus wherein the virus is multiply substituted, such as at the various NIm sites of HRV.

In an analogous manner, HRV14 chimeras were constructed in which the NIm-1A loop of HRV14 was replaced with two variations of residues 735–752 of the HIV-1 gp41 antigen having the following sequences:

| gp41 735–752 | | DRPEGIEEEGGERDRDRS | |
|---|---|---|---|
| HRV14:HIV gp41 I | IQN | PEGIEEEGGERDRDRS | KLF |

The variations of the HRV14:HIV gp41 chimera differ only in the sequence of amino acids bordering the loop region of HRV14 NIm-IA. In chimera I, the two preceding residues (QN) are those found in the wild-type HRV14 sequence, and in chimera II, the DR sequence resembles that of the analogous portion of a poliovirus 1 Sabin:HIV gp41 chimera (Evans, et al., *Nature*, 339:385–388, 1989), which was able to stimulate rabbit polyclonal antisera capable of neutralizing diverse strains of HIV-1.

The plasmid pWR40:HIV MN19 substituted at the NIm-IA site with a sequence encoding the gp120 immunodominant loop, as described in Example 3, and pWR40 containing a complete cDNA sequence of HRV14 have been deposited for 30 years at the American Type Culture Collection (ATCC) in Rockville, Md. and assigned Accession Nos. ATCC VR X and ATCC VR Y, respectively.

The present invention is not to be limited in scope by the virus-encoding plasmid deposited, since the deposited embodiment is intended to serve as a single illustration of one aspect of the invention and any plasmids or viruses which are functionally equivalent are within the scope of this invention. The deposit of material does not constitute an admission that the written description contained herein is inadequate to enable the practice of any aspect of the invention, including the best mode, or is the deposit to be construed as limiting the scope of the claims to the specific illustrations that they represent. In point of fact, it will become apparent to those of skill in the art that various modifications of the invention, in addition to those shown and described herein, are readily possible. It is intended that such modifications fall within the scope of the appended claims.

We claim:

1. Biologically pure recombinant chimeric human rhinovirus constructed by inserting into the human rhinovirus 14 (HR14) nucleotide sequence encoding part of a neutralizing immunogenic site, a heterologous nucleotide sequence encoding the chimeric region, wherein the chimeric region is expressed on the surface of the chimeric rhinovirus and is capable of participating in an immune reaction.

2. The rhinovirus of claim 1, wherein the neutralizing immunogenic site is NIm-II.

3. The rhinovirus of claim 2, wherein the chimeric region is presented in viral protein VP 2 of NIm-II.

4. The rhinovirus of claim 3, wherein the chimeric region is presented from about amino acid 157 to about amino acid 165 of VP 2.

5. The rhinovirus of claim 1, wherein the neutralizing immunogenic site is NIm-IA.

6. The rhinovirus of claim 5, wherein the chimeric region is presented in viral protein VP 1 of NIm-IA.

7. The rhinovirus of claim 6, wherein the chimeric region is presented from about amino acid 85 to about amino acid 96 of VP 1.

8. The rhinovirus of claim 1, wherein the chimeric region is of viral origin.

9. The rhinovirus of claim 8, wherein the chimeric region is derived from a site selected from the group consisting of a neutralizing immunogenic site and a cellular receptor site.

10. The rhinovirus of claim 8, wherein the viral origin of the chimeric region is an orthomyxovirus.

11. The rhinovirus of claim 10, wherein the orthomyxovirus is influenza virus.

12. The rhinovirus of claim 11, wherein the chimeric region is from the hemagglutinin antigen of the influenza virus.

13. The rhinovirus of claim 12, wherein the chimeric region is from about amino acid 128 to about amino acid 136 of the hemagglutinin antigen.

14. The rhinovirus of claim 8, wherein the viral origin of the chimeric region is a picornavirus.

15. The rhinovirus of claim 14, wherein the picornavirus is poliovirus.

16. The rhinovirus of claim 15, wherein the chimeric region is from the NAg-1 site of the poliovirus.

17. The rhinovirus of claim 16, wherein the chimeric region is from about amino acid 93 to about amino acid 100 of the NAg-1 site.

18. The rhinovirus of claim 15, wherein the polio virus is type 3.

19. The rhinovirus of claim 8, wherein the viral origin of the chimeric region is a retrovirus.

20. The rhinovirus of claim 19, wherein the retrovirus is a human immunodeficiency virus.

21. The rhinovirus of claim 20, wherein the human immunodeficiency virus is selected from the group consisting of HIV-1 and HIV-2.

22. The rhinovirus of claim 20, wherein the chimeric region of the human immunodeficiency virus is selected from the gag or env proteins.

23. The rhinovirus of claim 1, wherein the chimeric region is of non-viral origin.

24. The rhinovirus of claim 23, wherein the chimeric region is derived from a source selected from the group consisting of a neoplasm, a parasite, and a bacterium.

25. The rhinovirus of claim 1, wherein multiple neutralizing sites of the chimeric rhinovirus contain a chimeric region.

26. The rhinovirus of claim 25, wherein the chimeric region at each neutralizing site is different.

* * * * *